US00PP18639P2

(12) United States Plant Patent
Goffreda et al.

(10) Patent No.: US PP18,639 P2
(45) Date of Patent: Mar. 25, 2008

(54) APRICOT TREE NAMED 'NJA150'

(50) Latin Name: *Prunus armeniaca L.*
Varietal Denomination: NJA150

(75) Inventors: Joseph C. Goffreda, Millstone Township, NJ (US); Anna M. Voordeckers, East Windsor Township, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 11/482,587

(22) Filed: Jul. 6, 2006

(51) Int. Cl.
*A01H 5/00* (2006.01)

(52) U.S. Cl. ..... Plt./186
(58) Field of Classification Search ..... Plt./186
See application file for complete search history.

*Primary Examiner*—Kent Bell
(74) *Attorney, Agent, or Firm*—Klarquist Sparkman, LLP

(57) ABSTRACT

A new and distinct apricot variety of *Prunus armeniaca* named 'NJA150' is provided. This variety is distinguished from other apricot varieties known to the inventors by its unique combination of fruit that ripens in mid-season, attractive fruit with a flat apex and a yellow-orange color, freestone fruit that is juicy and that has a fine, melting texture and moderately acidic flavor, and good production of fruit.

6 Drawing Sheets

Latin name of genus and species of the plant claimed: *Prunus armeniaca* L.

BACKGROUND OF THE INVENTION

The present invention relates to a new and distinct variety of apricot tree named 'NJA150'. Our new tree resulted from crossing 'NJA103' (unpatented) as the seed parent with 'NJA45' (unpatented) apricot tree, as the pollen parent. The new variety differs from seed parent, 'NJA103' in that the new variety produces fruit with yellow-orange flesh, while the seed parent produces fruit with orange flesh. The new variety differs from pollen parent 'NJA45' in that the new variety has larger fruit with a fine flesh texture, while the pollen parent has small fruit with flesh that has prominent fibers. The resulting tree was selected when growing in a cultivated area at the Rutgers Fruit Research and Extension Center in Cream Ridge, N.J.

BRIEF SUMMARY OF THE INVENTION

The 'NJA150' variety is distinguished from other apricot varieties due to the following unique combination of characteristics: attractive round fruit with a flat apex, fruit with an attractive yellow orange color, good production of fruit that ripe in mid-season, and fruit that is freestone, has an average to above average eating quality, is juicy and with a fine, melting texture.

The variety was asexually reproduced at the Rutgers Fruit Research and Extension Center in Cream Ridge, N.J. Asexual reproduction of this new variety by budding onto 'Lovell' rootstock (unpatented) shows that the foregoing characteristics are fixed.

The following detailed description concerns the original tree, 'NJA150'. The original tree and asexual progeny have been observed growing in a cultivated area Upper Freehold Township, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The Royal Horticultural Society (R.H.S.) Colour Chart.

BRIEF DESCRIPTION OF THE DRAWINGS

This new variety is illustrated by the accompanying photographic drawings, depicting the apricot tree by the best possible color representation using color photography. The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

Figure 1:
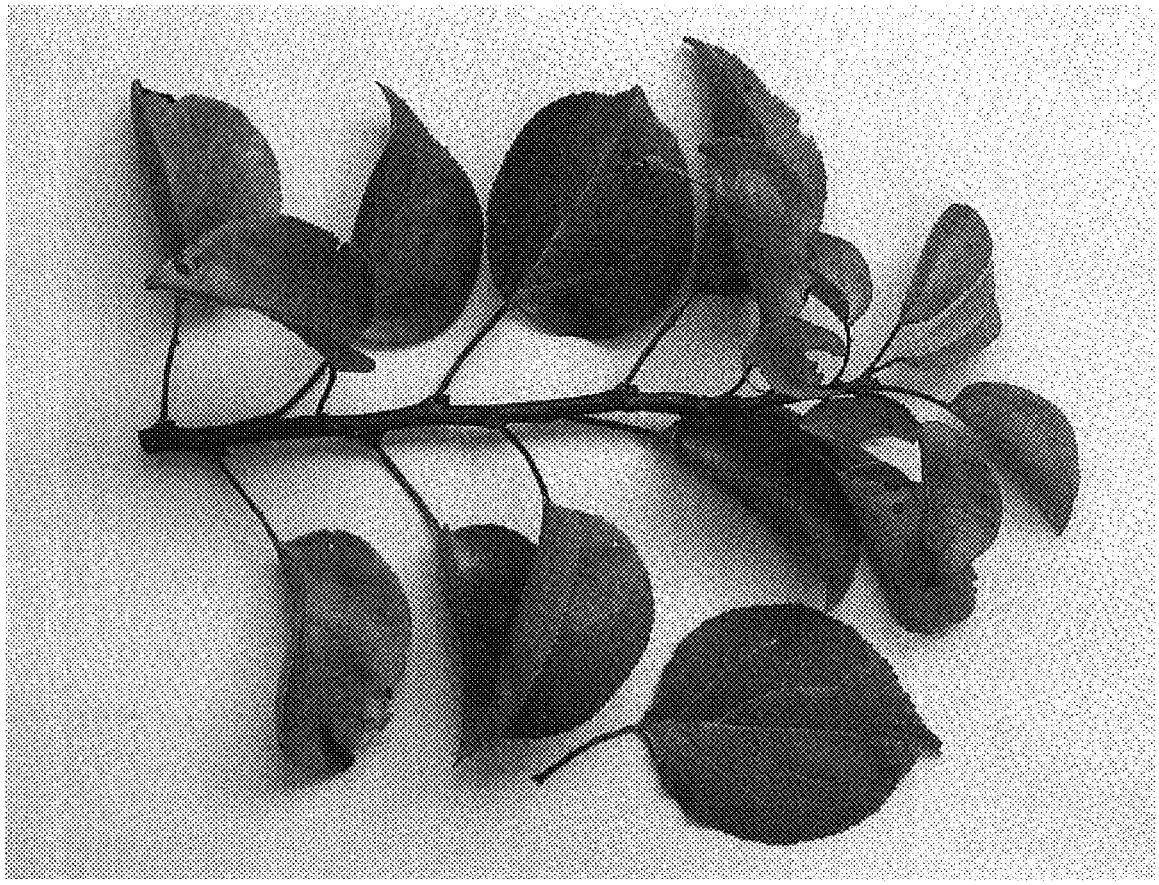
FIG. 1 is a color photograph taken on Sep. 21, 2004 of a characteristic twig of 'NJA150' in late summer bearing typical leaves of the mature and immature foliage.
Figure 2:
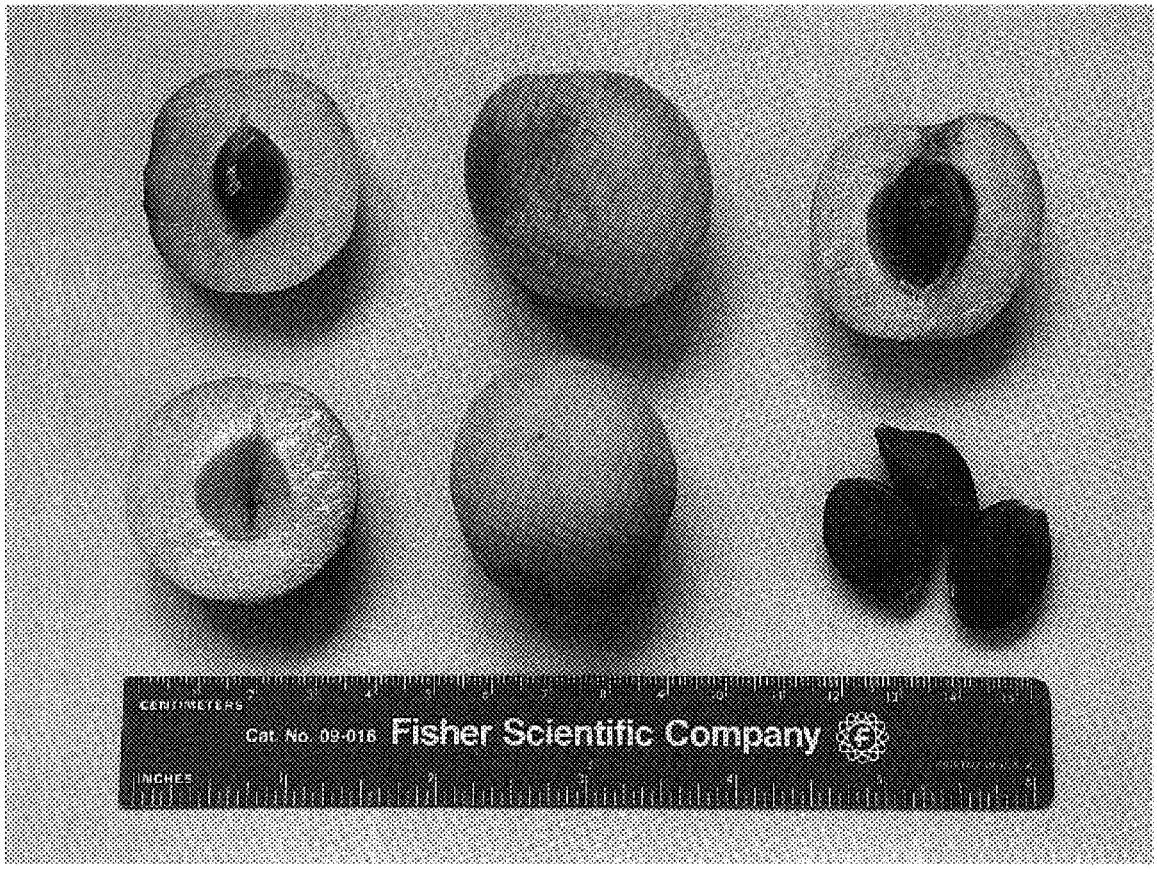
FIG. 2 is a color photograph taken on Jul. 19, 2005 of characteristic mature fruit and stones of 'NJA150'. Whole fruit are presented in two positions and transverse and longitudinal cross sections to show that the pericarp generally does not adhere to the pit when the fruit is mature. The stones illustrate the elliptoid shape and the generally smooth surface of the stone.
Figure 3:
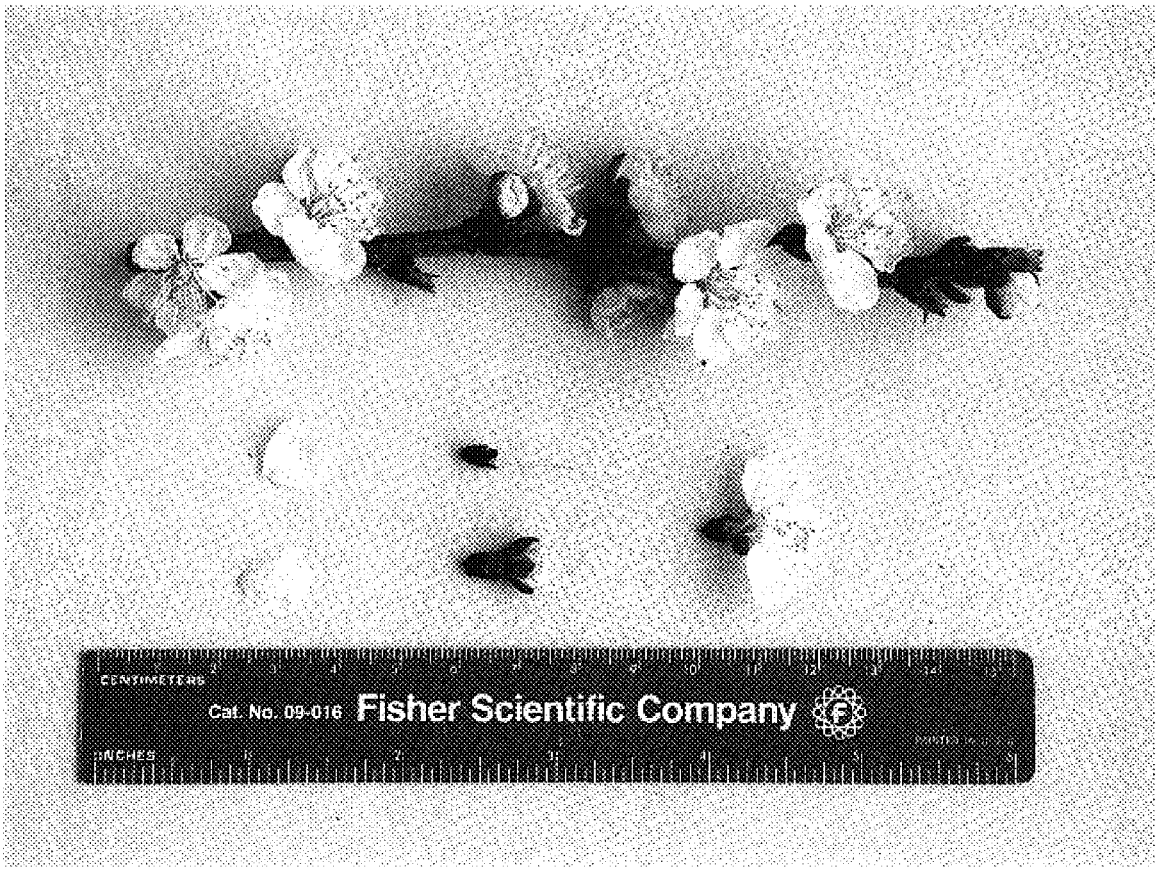
FIG. 3 is a color photograph taken on Apr. 15, 2005 of a characteristic twig that illustrates the typical flower buds and large, showy flowers of 'NJA150'.
Figure 4:
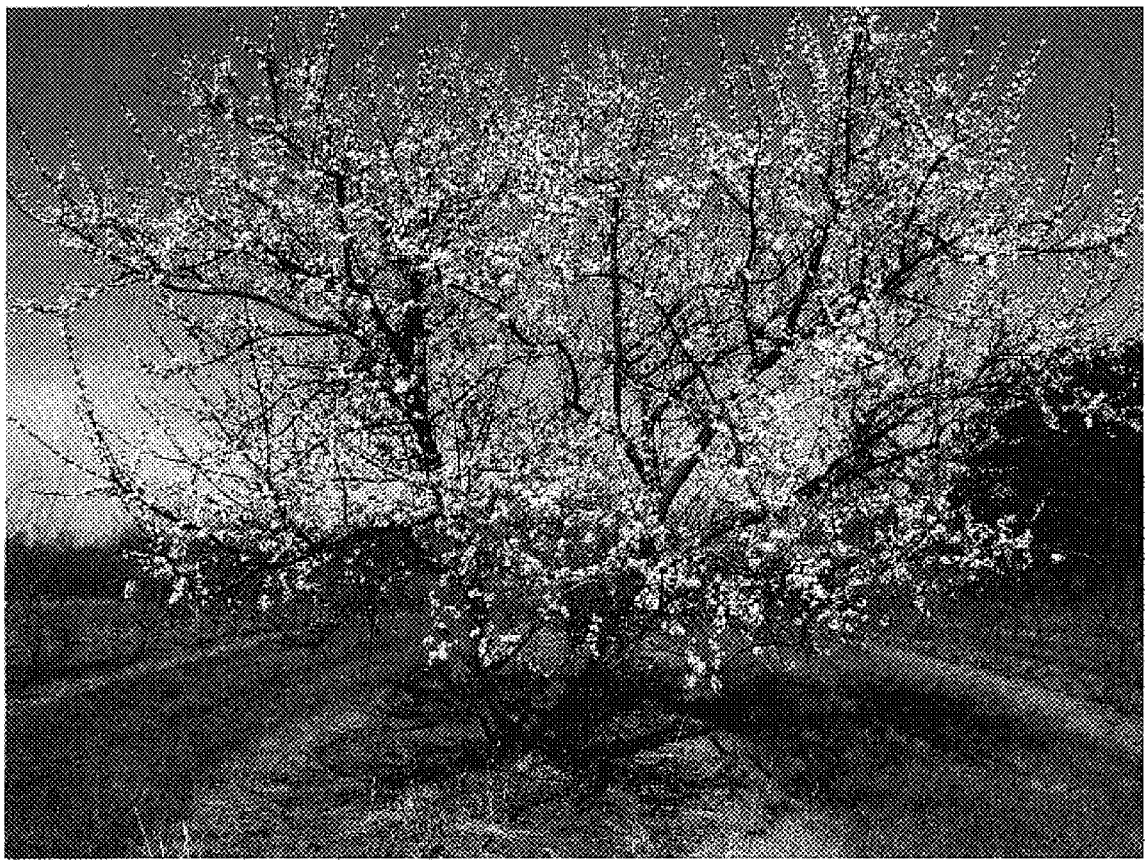
FIG. 4 is a color photograph taken on Apr. 14, 2005 of a tree of 'NJA150' in early spring that illustrates the spreading growth habit of the tree and the attractive showy blooms.
Figure 5:
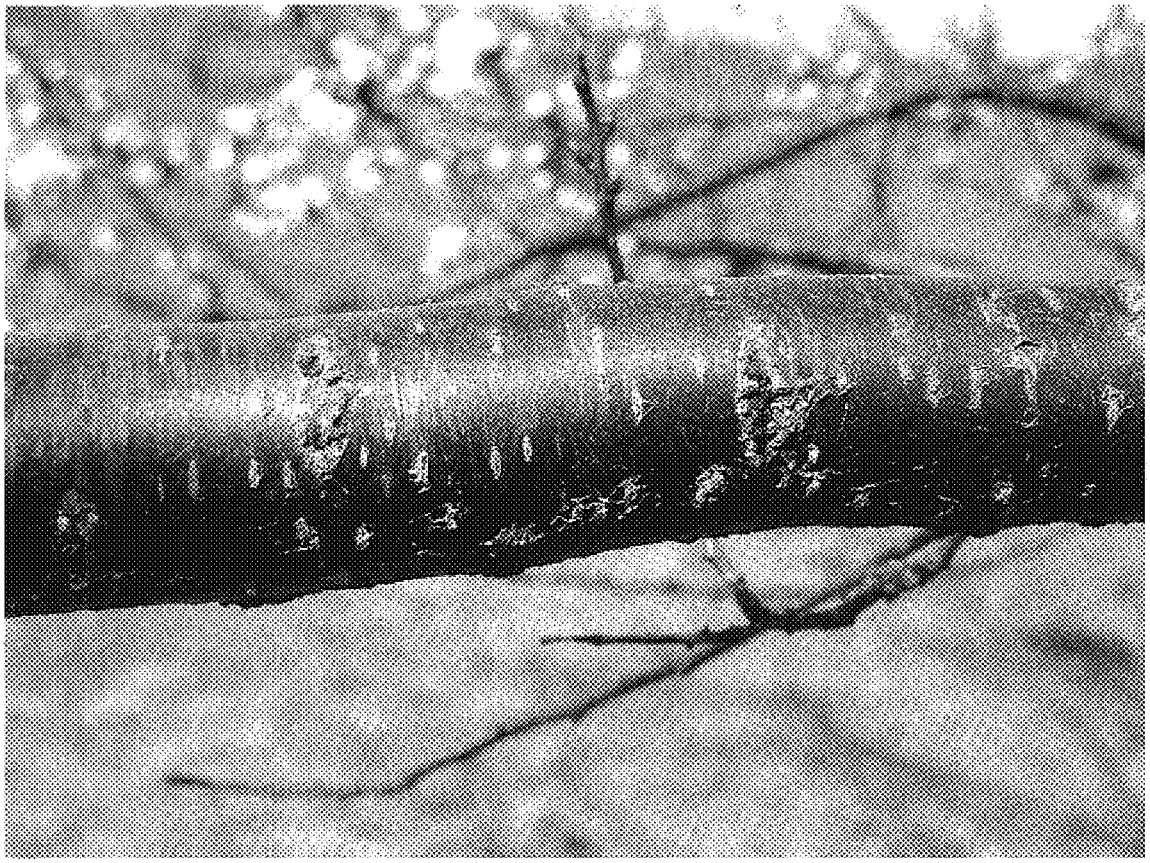
FIG. 5 is a color photograph taken on Apr. 9, 2004 of immature bark of 'NJA150' that illustrates color and the moderate density of elliptical greyed-white lenticels on the immature bark.
Figure 6:
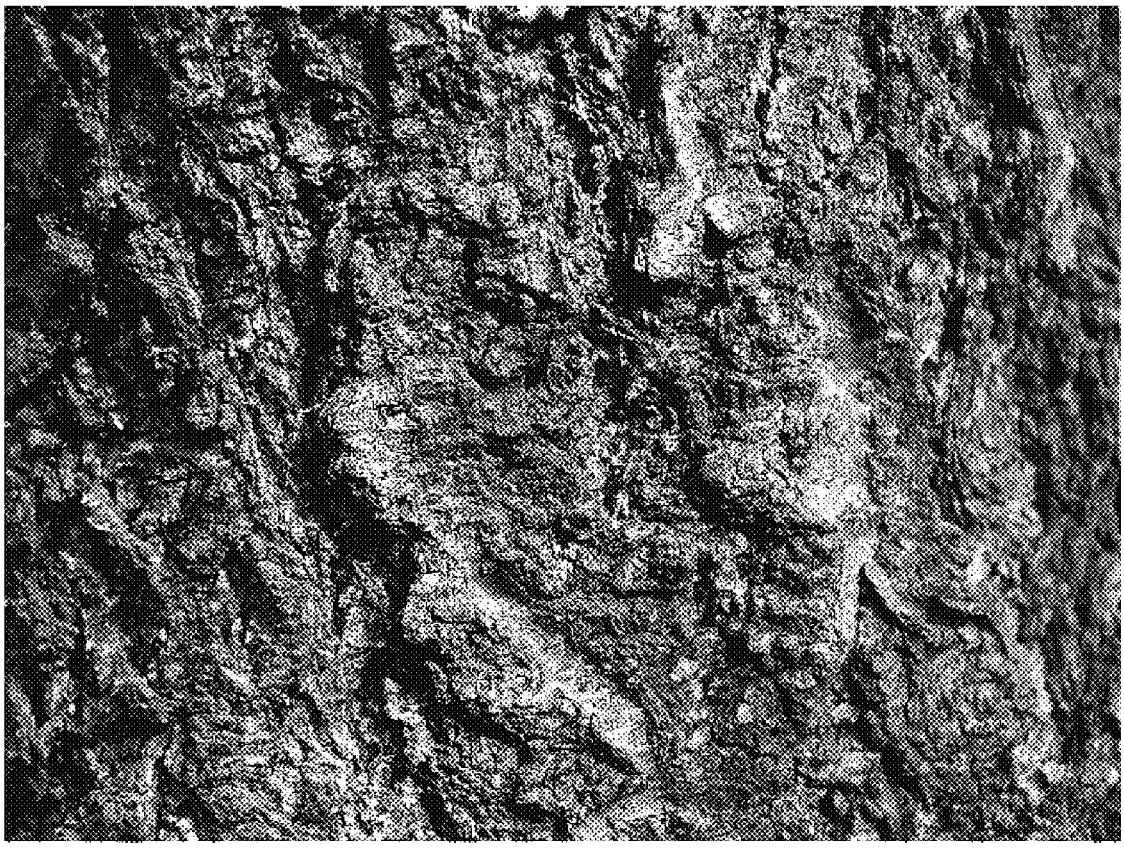
FIG. 6 is a color photograph taken on Oct. 27, 2005 of mature bark of 'NJA150' that illustrates the rough texture of the mature bark.

The following detailed description of the 'NJA150' variety is based on observations of the original tree. The observations of flowers, fruit, and leaves were of a representative sampling of such leaves from the original tree. The observed tree was 10 years of age and growing on its own roots in a research field located in Upper Freehold Township, N.J.

Scientific name: *Prunus armeniaca* L.

Parentage:

*Seed parent.*—Apricot tree named 'NJA103'.

*Pollen parent.*—Apricot tree named 'NJA45'.

Tree:

*Vigor.*—Vigorous.

*Plant hardiness zone.*—Growth of plants has only been observed in zone 6*b*.

*Dormant flower bud cold tolerance.*—At least to −20° C.

*Overall shape.*—Spreading.

*Height.*—Above average as compared to other apricot cultivars. For example, measurement of the original tree of the new variety on its own roots at ten years after planting shows an average height of 6.1 meters when grown in Cream Ridge, N.J.

*Width.*—Above average as compared to other apricot cultivars. For example, measurement of the original tree of the new variety on its own roots at ten years after planting shows an average width of 7.4 meters when grown in Cream Ridge, N.J.

*Caliper.*—Ten year old original tree of the new variety is 92 cm in circumference measured at 15 cm from the ground.

Trunk and branches:

*Trunk bark texture.*—Rough.

*Trunk bark color.*—Greyed-green (between RHS 197*a* and RHS 197*b*).

*Primary branches.*—Branches that are approximately 15 cm in circumference are greyed-red (between RHS 178*a* and RHS 178*b*) in color. Typical primary branch length is between 2 and 3 m, averaging about 2.6 m.

*Lenticels.*—Moderate density, approximately 2 per square cm; elliptical shape; typical examples of which measured 4.5 mm in length and 1.7 mm in width; greyed-white (between RHS 156*a* and RHS 156*b*) in color.

*Branch pubescence.*—None.

*New growth bark.*—Color varies between greyed-orange (RHS 176*a*) and greyed-purple (RHS 183*a*) in sun to greyed-orange (between RHS 165*a* and RHS 165*b*) in shade.

*Internodes.*—Length averaging 13.6 mm on a one-year shoot.

*Amount of growth per season.*—A typical branch produces between 0.5 and 0.8 m of growth per season, averaging about 0.65 mm.

Leaves:

*Texture.*—Glabrous.

*Sheen.*—Young leaves semi-glossy with a flat finish on the underside.

*Length.*—About 97 mm to 116 mm, averaging about 109 mm including the petiole.

*Width.*—About 61 mm to 80 mm, averaging about 71 mm.

*Petiole.*—Average 30.4 mm long and about 2.0 mm in diameter.

*Margin.*—Serrate.

*Margin undulation.*—Nearly none.

*Form.*—Ovate.

*Apex.*—Abruptly acuminate, curved downward.

*Base.*—Broadly obtuse to truncate.

*Venation.* —Pinnate.

*Glands.*—Number: About 0 to 2, averaging about 1. Position: Located on the leaf margin and petiole. Size: Length averaging 0.85 mm and width averaging 0.85 mm. Form: Globose.

*Stipules.*—None observed on mature leaves.

*Leaf color.*—Upper leaf surface: Yellow-green (between RHS 146*a* and RHS 147*a*). Lower leaf surface: Yellow-green (RHS 148*b*). Vein: Greyed-yellow (RHS 160*c*). Petiole: Greyed-purple (RS 184*a*).

*Pubescence.*—None.

Flowers:

*Size.*—Large size, somewhat showy because of their size, typical flower measuring between 26.7 mm to 30.1 mm, averaging about 28.6 mm across. Typical flower depth is between 18 and 20 mm, averaging about 19 mm.

*Color.*—Dormant bud: Brown (between RHS 200*a* and RHS 200*b*). Pink stage bud: Red-purple (RHS 62*d*). Open flower: Young open flowers red (RHS 36*d*) becoming white (RHS 155*d*) prior to petal fall.

*Petals.*—Typically five petals per flower; cupped and round in shape; averaging about 13.0 mm long and 13.0 mm wide. Between red (RHS 36*d*) and white (RHS 155*d*) in color on both the upper and lower surfaces.

*Petal apex.*—Rounded.

*Petal base.*—Acute.

*Stamens.*—Number: Variable, 24 to 29, averaging about 25. Length: Variable, between 5.2 mm to 6.3 mm, averaging 5.6 mm. Filament color: White (RHS 155*b*). Anther color: Yellow (RHS 12*c*).

*Pistil.*—Number: One. Size: Length between 17.7 mm and 20.5 mm, averaging about 18.9 mm. Pistil color: Yellow-green (RHS 145*c*). Ovary: Ellipsoid in shape and covered with long pubescence.

*Sepals.*—Number: Five. Pubescence: None. Color: Greyed-yellow (RSH 160*c*) with a greyed-red (between RHS 180*a* and RHS 180*b*) over color on both the upper and lower surfaces. Shape: Triangular, with a rounded apex. Margin is entire. Size: length averaging 6.4 mm, width averaging 2.6 mm.

*Nectar cup color.*—Orange (RHS 25*a*).

*Pollen.*—Abundant; yellow-orange (RHS 20*a*) in color.

*Fragrance.*—Moderate aroma.

*Bloom season.*—Onset of bloom in 2005 on April 11; full bloom on April 15.

Fruit:

*Size.*—Small to medium, averaging about 4.0 cm long, 4.1 cm wide parallel to the suture and 4.0 cm wide perpendicular to the suture.

*Typical weight.*—37g.

*Form.*—Longitudinal section: Round. Traverse section: Round.

*Suture.*—Very shallow, extending from the base to apex.

*Ventral surface.*—Typically smooth.

*Base.*—Round.

*Apex.*—Flat.

*Stem.*—Average length of 5.6 mm and an average diameter of 2.0 mm. Color varies between greyed-orange (RHS 176*a*) and greyed-purple (RHS 183*a*) in sun to greyed-orange (between RHS 165*a* and RHS 165*b*) in shade.

*Skin.*—Thickness: Average. Surface: Regular with short pubescence. Tenacity: Average. Astringency: None. Tendency to crack: Low. Color: Freckled greyed-red (between RHS 179*a* and RHS 179*b*) blush over a yellow (RHS 10*b*) ground color.

*Fruit properties.*—Flesh color: Yellow-orange (between RHS 14*d* and RHS 16*b*). Flesh adhesion: Generally freestone, tends to cling slightly at suture. Juice: Moderate. Texture: Fine, melting. Fibers: Not noticeable. Ripens: Mid-season, between June 30 and July 16 at Cream Ridge, N.J. Flavor: Average to above average, moderately acidic. Soluble solids: 17%. Aroma: Moderate. Eating quality: Good.

*Keeping quality.*—Average.

*Shipping quality.*—Below average.

*Usage.*—Dessert.

*Market.*—Fresh market.

*Productivity.*—Very good. Trees have produced a crop in 4 out of 5 years and a full crop in 3 out of 5 years at Cream Ridge, N.J.

*Fruit brix.*—Typically between 15 to 20%, averaging about 18%.

Stone:

*Type.*—Freestone.

*Form.*—Elliptoid.

*Base angle.*—Narrow.

*Apex angle.*—Narrow.

*Surface.*—No prominent markings.

*Ventral suture.*—Very low, extending from the base to the apex.

*Dorsal ridge.*—Nearly none.

*External color.*—Greyed-orange (between RHS 165*c* and RHS 165*d*).

*Internal color when cracked.*—Greyed-orange (between RHS 165*c* and RHS 165*d*).

*Cavity surface color.*—Greyed-orange (RHS 165*d*).

*Average stone dry weight.*—1.6 g.

*Average stone wall thickness.*—Varies between 1.6 and 4.2 mm.

*Size.*—Averages about 23.4 mm long, 17 mm wide parallel to the dorsal ridge, and 12.1 mm wide perpendicular to the dorsal ridge.

*Tendency to split.*—Low.

*Kernel.*—Form: Ovoid. Skin color: Greyed-orange (RHS 165*b*). Vein color: Greyed-orange (RSH 165*a*). Viability: Yes. Dry weight: 0.5 g. Size: Averages about 16.2 mm long, 9.9 mm wide, and 6.7 mm in breadth.

Plant/fruit disease and pest resistance/susceptibility: No atypical resistance/susceptibilities have been noted.

We claim:

1. A new and distinct variety of apricot tree, substantially as herein shown and described.

* * * * *